United States Patent [19]

Schulte-Elte et al.

[11] Patent Number: 4,460,792
[45] Date of Patent: Jul. 17, 1984

[54] PROCESS FOR THE PREPARATION OF DELTA- AND EPSILON-DAMASCONES

[75] Inventors: Karl H. Schulte-Elte, Onex; Roger L. Snowden, Grand-Lancy; Bernard L. Muller, Geneva, all of Switzerland

[73] Assignee: Firmenich S.A., Geneva, Switzerland

[21] Appl. No.: 409,516

[22] Filed: Aug. 19, 1982

[30] Foreign Application Priority Data

Sep. 7, 1981 [CH] Switzerland .................. 5741/81
Oct. 15, 1981 [CH] Switzerland .................. 6597/81

[51] Int. Cl.³ .................. C07C 45/67; C07C 45/51
[52] U.S. Cl. .................. 568/341; 568/361
[58] Field of Search .................. 568/341, 343, 403, 405, 568/361

[56] References Cited

U.S. PATENT DOCUMENTS 3,887,625 6/1975 Schulte-Elte .................. 568/393
3,976,700 8/1976 DeSimone .................. 568/301

Primary Examiner—James H. Reamer
Attorney, Agent, or Firm—Pennie & Edmonds

[57] ABSTRACT

Useful perfumery ingredients delta- and epsilon-damascone are prepared by a process which consists in an anionic cleavage, in the presence of a strong base of a diallyl alcohol of formula

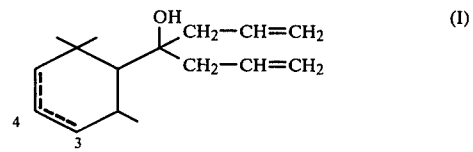

wherein the dashed lines in position 3 or 4 of the ring designate a double bond, followed by an isomerization of the terminal double bond of the thus obtained product by means of an acidic isomerizing agent.

6 Claims, No Drawings

PROCESS FOR THE PREPARATION OF DELTA- AND EPSILON-DAMASCONES

BRIEF SUMMARY OF THE INVENTION

The instant invention relates to a new process for the preparation of delta- and epsilon-damascone under either one of their isomeric cis- or trans-forms, which process consists in (a) treating with a strong base in an inert organic solvent a diallyl carbinol of formula

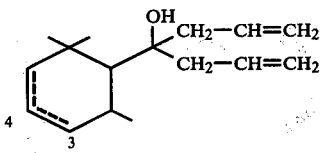

wherein the dashed lines in position 3 or 4 of the ring designate a double bond, and subsequently (b) isomerizing the terminal double bond of the thus obtained product by means of an acidic isomerizing agent.

BACKGROUND OF THE INVENTION

Since their discovery, approximately ten years ago, cycloaliphatic ketones known under the designation of δ- and ε-damascone have been the object of a number of scientific publications [see e.g. J. Chem. Soc., Perkin-Trans. (1975) 1727-36; Tetrahedron Letters 515 (1975); Chem. Comm. 161 (1973)]. Delta-damascone especially has found a utility in perfumery [see Swiss Pat. No. 566,112], wherein it is used to develop notes reminiscent of those shown by its α- and β-isomers, without possessing however their fineness and their elegance and consequently their broad range of utility.

The prior art teaches a process for the preparation of δ-damascone, which process consists in the addition of 1,3-pentadiene to mesityl oxide and in the subsequent condensation in a basic medium of the obtained product with acetic anhydride followed by water elimination.

The said process is illustrated hereinbelow:

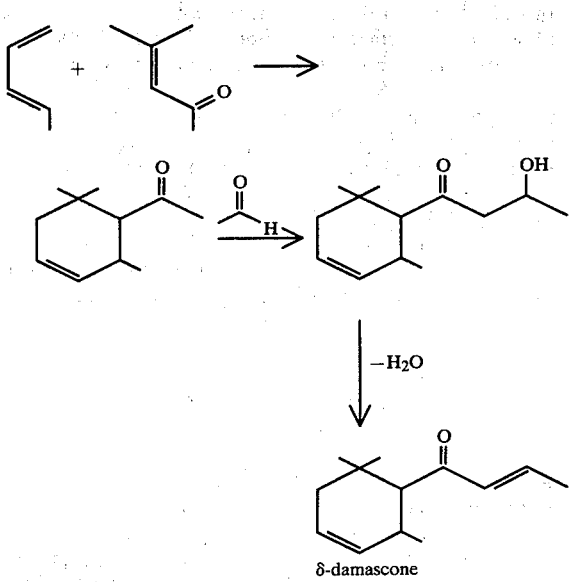

[see Chem. Comm. 161 (1973)].

The above given process enables to prepare trans δ-damascone under its two cyclanic isomeric forms of formula

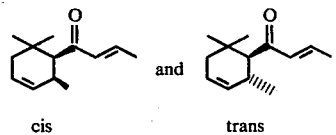

Their separation can be effected by means of preparative vapour phase chromatography.

Another process for preparing δ-damascone has been disclosed in Tetrahedron Letters 515 (1975):

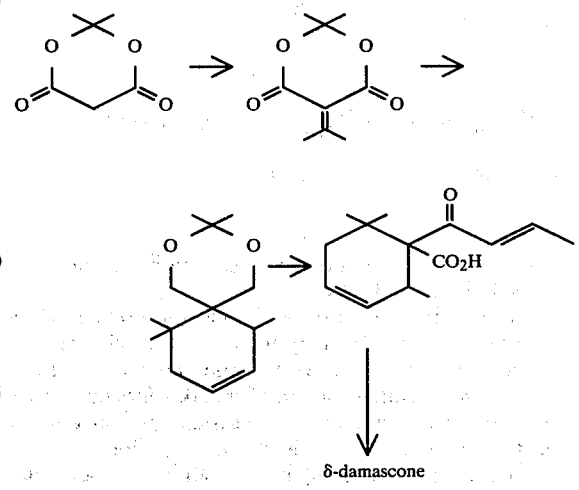

The instant invention provides a novel process to prepare both δ- and ε-damascone under either one of their cyclanic isomeric forms.

PREFERRED EMBODIMENTS OF THE INVENTION

The process of the present invention consists in treating by means of a strong base in an inert organic solvent a diallyl carbinol of formula

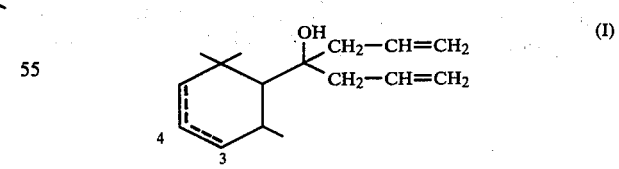

wherein the dashed lines in position 3 or 4 designate a double bond, and subsequently isomerizing the terminal double bond of the thus obtained product by means of an acidic isomerizing agent.

The compounds of formula (I), used as starting materials in the above said process can be obtained in accordance with the process illustrated hereinbelow:

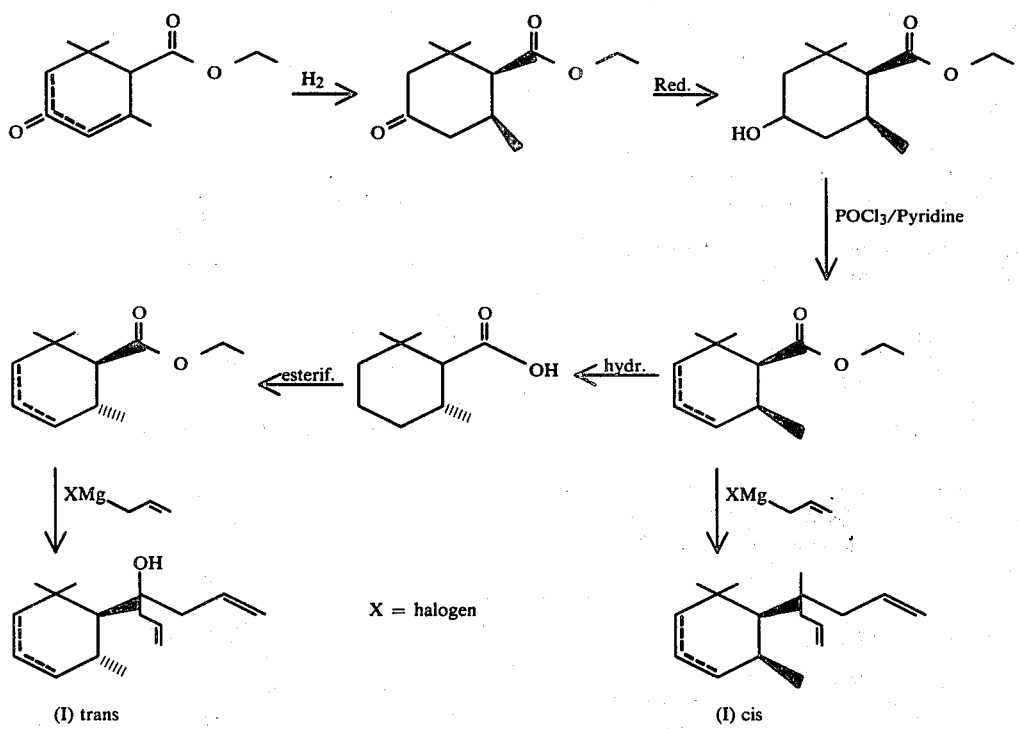

(I) trans (I) cis

The details of the process used will be given in the example which follows.

The reaction which characterizes the process of the invention consists formally in an anionic splitting promoted by a strong base. To this end, mineral or organic bases such as alkali metal hydrides, alkoxides or hydroxides, preferably sodium or potassium derivatives, are used. Among the said bases one may cite especially sodium or potassium hydride, sodium or potassium tert-butoxide, sodium tert-amylate and sodium methoxide or ethoxide.

The choice among the bases cited above is determined by considerations of economy, safety and occupational health. As a consequence, alkoxides are preferred to hydrides, and among them potassium or sodium tert-butoxide is preferably used.

It could be established that the proportion of the base used must be equal to or higher than the required stoichiometric quantity. In reality, the best yields were achieved by the use of an excess of base.

The reaction times observed are relatively short. To this effect, we should note that the conversion of allylic carbinols into their corresponding damascones or damascenones derivatives (I), according to the instant invention, takes place via the formation of an enolate of formula

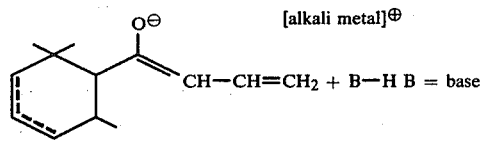 $\text{CH—CH=CH}_2$ + B—H  B = base which compound is unstable in protic media, hence the necessity to stop rapidly the reaction when this is promoted for instance by an alkoxide. Thus at temperatures of between about 20° and 70° C., the reaction times can be of the order of a few minutes when sodium or potassium tert-butylate is the base. When sodium hydride is used instead, the reaction time is longer; for instance, by making use of potassium hydride, 15 hours are necessary to convert 2,6,6-trimethyl-1-[4-hydroxyhepta-1,6-diene-4-yl]-cyclohex-2-ene into δ-damascone in a mixture of tetrahydrofuran and phosphorus hexamethyltriamide. Of course, the temperature exerts a determining influence on reaction times. The process, which in itself is exothermic, can be carried out at a temperature near the room temperature. Values of between about 20° and 70° C. are preferred. At lower temperatures, the reaction times become too long, whereas at temperatures higher than the above given upper limit, we have observed the formation of undesired by-products.

As described above, the reaction is effected in an inert organic solvent. Suitable solvents include ethers such as tetrahydrofuran or diisopropyl-ether, amides such as dimethylformamide or phosphorus hexamethyl-triamide, an aromatic hydrocarbon, for instance benzene or toluene, an alcohol such as ethyl alcohol or tert-butanol, or even methyl-pyrrolidone or dimethylsulfoxide. Mixtures of the above cited solvents can also be used. According to a preferred embodiment, potassium tert-butoxide is used as base and dimethylformamide or a mixture of dimethylformamide with tetrahydrofuran can be used as a solvent.

Step (b) of the process of the present invention, which consists in isomerizing the terminal double bond of the compounds obtained by the anionic cleavage of allylic alcohols (I), is carried out according to known methods, for instance by treating them in accordance with the process described in Swiss Pat. No. 537,352.

The invention is illustrated in a more detailed manner by the following example wherein the temperatures are given in degrees centigrade and the abbreviations have the meaning common in the art.

EXAMPLE

Preparation of δ- and ε-damascone
The method followed was the following:
30 g (0.128M) of the chosen allylic alcohol (I) have been added in a single portion, at room temperature and under a nitrogen atmosphere, to a suspension of 20.6 g (0.184M) of potassium tert-butoxide in 260 ml of dimethylformamide. Upon addition of the allylic alcohol the temperature of the reaction mixture raises to about 40° while its color becomes brown-black.

The mixture is kept at room temperature for ½ h, whereupon it was poured onto ice and extracted with ether.

The combined organic extracts were subjected to the usual treatments of washing with a 10% HCl solution and with a sodium bicarbonate aqueous solution, drying and evaporation. This gave a mixture containing, together with the desired damascones, their corresponding "iso"-damascones.

The obtained results are summarized in the following Table.

| Starting Material | End product | % (by weight) |
| --- | --- | --- |
| OH (structure) | O (structure) | 18 |
|  | O (structure) | 11 |
|  | O (structure) | 14 |
|  | O (structure) | 27 |
| OH (structure) | O (structure) | 30 |
|  | O (structure) | 20 |
|  | O (structure) | 34 |
|  | O (structure) | 16 |

The mixture thus obtained was then diluted in 220 ml of toluene and heated to reflux during 1 h under a nitrogen atmosphere in the presence of 0.2 g of p-toluene-sulfonic acid. It was thus possible to isomerize completely iso-damascones into their corresponding damascones. The reaction mixture was poured onto ice and extracted twice with ether, then the combined organic extracts were washed as usual with a $NaHCO_3$ aqueous solution until neutrality. δ- And ε-damascones were obtained after drying, evaporation and distillation of the resulting residue. The obtained compounds were separated one from the other by preparative vapour phase chromatography.

cis-ε-damascone
  IR: 3060, 1670, 1640, 1620 and 970 $cm^{-1}$;
  NMR (90 MHz; $CDCl_3$): 1.04; 0.92 and 1.1; 1.85; 2.76; 5.5–6.8 δ ppm;
  MS: $M^+ = 192(10)$; m/e: 177(4), 163(1), 149(3), 137(4), 123(30), 109(9), 93(6), 81(22), 69(100), 55(7), 41(38).

cis-δ-damascone
  IR: 3040, 1670, 1660, 1620 and 970 $cm^{-1}$;
  NMR (90 MHz; $CDCl_3$): 0.95; 0.90 and 1.0; 2.75; 5.3–6.75 δ ppm;
  MS: $M^+ = 192$ (51); m/e: 177(32); 163(7); 149(10); 137(10); 123(48); 109(14); 93(7); 81(23); 69(100); 55(8); 41(27).

trans-ε-damascone
  IR: 3040, 1695, 1680, 1625 and 980 $cm^{-1}$;
  NMR (90 MHz; $CDCl_3$): 0.86 (d; J=7 Hz); 1.0 and 1.09 (2s); 2.45 (m); 5.34–5.70 (m); 6.02–7.0 (m) δ ppm;
  MS: $M^+ = 192(10)$ m/e: 177(6); 163(3); 149(5); 137(5); 123(30); 109(10); 93(7); 81(22); 69(100); 55(6); 41(40).

trans-δ-damascone
  IR: 3045, 1670, 1640, 1620 and 975 $cm^{-1}$;
  NMR (90 MHz; $CDCl_3$): 0.84 (d; J=7 Hz); 0.90 and 0.94 (2s); 1.90 (dxd; J=8 and 2 Hz); 2.48 (m); 5.5 (m); 6.18 and 6.82 (2m) δ ppm;
  MS: $M^+ = 192(45)$; m/e: 177(24); 163(8); 149(10); 137(10); 123(50); 109(12); 93(10); 81(20); 69(100); 41(20).

The allylic alcohols used as starting materials in the above described process can be prepared as follows:

a. 246 g (1.17M) of ethyl 2,6,6-trimethyl-4-oxo-cyclohex-2-en-1-carboxylate [see J. Org. Chem. 27, 3886 (1962) and J. Org. Chem. 35, 1053 (1970)] were hydrogenated at 18°–20° in 2 l of cyclohexane in the presence of 5 g of palladium on charcoal. After 15 h, the mixture had absorbed 28 l of hydrogen and it was filtered, whereupon the clear filtrate was evaporated to give on distillation on a Vigreux column 240 g of a white oil, b.p. 60°/0.05 Torr (yield 97%) consisting of ethyl 2,6,6-trimethyl-4-oxo-cyclohexane-1-carboxylate.

b. 56 g (1.47M) of $NaBH_4$ in 300 ml of water were added dropwise under nitrogen atmosphere to 311 g (1.47M) of the ester obtained under letter a. above in 1.5 l of ethanol. The temperature of the reaction mixture raised during the addition to 30°–35°. After having been left under stirring for 4 additional hours, the mixture was evaporated under reduced pressure and the resulting residue was poured into water, then extracted with ether. After the usual treatments of the combined ethereal extracts followed by evaporation, a residue was obtained which by fractional distillation gave 307 g of a white oil having b.p. 79°–82°/0.1 Torr (yield 95%) and consisting of ethyl 2,6,6-trimethyl-4-hydroxy-cyclohexane-1-carboxylate under its two isomeric forms

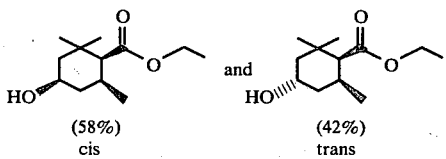

(58%) cis     (42%) trans

The two isomers could be separated by gas chromatography.

isomer cis
IR: 3425 and 1710 cm$^{-1}$;
NMR (90 MHz; CDCl$_3$): 0.90; 0.88 and 1.21; 1.25; 4.08; 4.18 δ ppm;
MS: m/e: 196(5), 181(20), 169(4), 153(10), 140(8), 123(78), 107(29), 101(14), 82(100), 68(40), 55(38), 41(54).

isomer trans
IR: 3475 and 1720 cm$^{-1}$;
NMR (90 MHz; CDCl$_3$): 0.95; 0.96 and 1.02; 1.28; 3.75 and 4.12 δ ppm;
MS: M$^+$=214(1); m/e: 196(26), 181(5), 169(16), 150(34), 139(11), 123(88), 107(68), 101(14), 82(100), 69(51), 55(52), 41(75).

c. 1.69 (1.1M) of phosphorous oxychloride were added dropwise during 5 h to a mixture kept at 0°–5° of the esters obtained under letter b. above (210 g; 0.98M) in 1 l of anhydrous pyridine. After having been left at room temperature for 1 additional hour, the mixture was poured onto ice and acidified then to pH 2 with 10% aqueous HCl, then extracted with ether. The usual treatments followed by distillation on a Vigreux column gave 150 g of an oily substance having b.p. 67°–72°/0.07 Torr (yield 78%).
IR: 1720, 1640, 720 and 690 cm$^{-1}$;
NMR (60 MHz; CDCl$_3$): 0.90–1.15; 1.28; 4.14; 5.2–5.9 δ ppm;
MS: M$^+$=196(27); m/e: 150(32), 123(89), 107(100), 91(22), 82(65); 68(33), 53(21); 41(45).

d. A solution of 30.6 g (0.4M) of allyl chloride and 30 g (0.153M) of the esters obtained according to paragraph c. above in 250 ml of anhydrous THF was added dropwise under nitrogen to a mixture of 8.4 g (0.35M) of magnesium turnings and some crystals of iodine in 50 ml of anhydrous THF, then the mixture was refluxed for 2 h. After having been left at room temperature for 2 h, the reaction mixture was poured onto ice and extracted twice with ether. The combined organic extracts were subjected to the usual treatments of washing with a saturated solution of ammonium chloride, drying and concentration to give a residue which upon distillation on a Vigreux column gave 30 g of a fraction at b.p. 57°–61°/0.03 Torr (yield 84%) consisting of a mixture of cis-4-[2,6,6-trimethylcyclohex-3-enyl]-4-hydroxy-hepta-1,6-diene and cis-4-[2,6,6-trimethylcyclohex-4-enyl]-4-hydroxy-hepta-1,6-diene whose analytical characteristics were the following:
IR: 3575 and 1640 cm$^{-1}$;
NMR (90 MHz; CDCl$_3$): 1.15 and 1.21; 1.25; 4.95–6.2 δ ppm;
MS: me/: 193(8), 151(3), 123(18), 111(13), 95(4), 83(23), 69(100), 55(10), 41(64).
IR: 3575 and 1620 cm$^{-1}$;
NMR (90 MHz; CDCl$_3$): 1.17; 1.19 and 1.29; 4.95–6.2 δ ppm;

MS: m/e: 193(6), 151(3), 123(16), 111(13), 95(3), 83(8), 69(100), 55(6), 41(55).

d′. 5 g (25.5 mM) of the mixture obtained according to the method c. above, have been heated at reflux under stirring and nitrogen atmosphere during 5 h together with 5.7 g (51 mM) of potassium tert-butoxide and 25 ml of dimethylsulfoxide. After cooling to room temperature, the mixture was poured onto ice and extracted twice with 30°–50° petrol ether. The organic phase gave after the usual treaments of washing and neutralization 0.5 g of residue.

The cooled alkaline mother liquors were acidified with conc. HCl and extracted with two fractions of ether. The combined ethereal phases were washed with brine, dried and concentrated to give 5 g of a raw material which by distillation on a bulb apparatus, gave 3.4 g of a mixture of trans-δ- and trans-ε-cyclogeranic acid.

e′. 3.5 g (20.8 mM) of the mixture obtained according to letter d′. above were heated to 180° in a sealed tube during 17 h with 7.0 g (47.3 mM) of triethyl ortho-formate. 3.5 g of SiO$_2$ and 10 ml of diethyl ether were added then to the cooled mixture and the whole was stirred for 1 h. After filtration and concentration, 2 g of Raney-nickel were added to the clear filtrate and the resulting mixture was stirred again for 1 h.

After filtration, the ethereal part was evaporated to give 4.4 g of a product which upon distillation in a bulb apparatus gave 3.4 g of a mixture essentially consisting of ethyl trans-δ- and trans-ε-cyclogeranate, accompanied by small quantities of the corresponding cis-isomers, which latter compounds can be separated by fractional distillation.

The obtained mixture of ethyl trans-δ- and trans-ε-cyclogeranate was directly used for the following reaction step.

f′. A solution of 3.5 ml (42.6 mM) of allyl chloride and 3.1 g (15.8 mM) of the mixture of esters obtained according to paragraph e′. above in 30 ml of anhydrous THF was added dropwise under nitrogen to a mixture of 0.906 g of magnesium turnings and some crystals of iodine in 5 ml of anhydrous THF. The mixture which during the addition warmed up till reflux, was cooled to room temperature, then it was again refluxed for 1 h. After the usual treatments (see paragraph d. above), it gave by distillation on a bulb apparatus 3.2 g of a mixture containing about 70% of the desired allylic alcohols.

An analytical sample was obtained by purifying the mixture by means of gas chromatography. The characteristics of the obtained sample were the following:
IR: 3560, 3080, 1640, 1015, 910 and 620 cm$^{-1}$;
NMR (60 MHz; CDCl$_3$): 1.1 and 1.12 (2d, J=6.5 Hz); 1.2–1.3 (2×2s); 2.2–2.65 (m); 4.8–6.8 (m); 5.6 (m); 5.73 (m) δ ppm;
MS: M$^+$=234(0); m/e: 216(3); 193(3); 151(3); 123(20); 111(16); 91(4); 81(8); 69(100); 41(60).

What we claim is:

1. A process for the preparation of δ- and ε-damascone which consists in
   (a) treating with at least a stiociometric amount of a strong base in an inert organic solvent a diallyl carbinol of formula

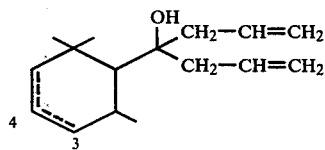 (I)

wherein the dashed lines in position 3 or 4 of the ring designate a double bond, and subsequently (b) isomerizing the terminal double bond of the thus obtained product by means of an acidic isomerizing agent.

2. Process according to claim 1, wherein a diallyl carbinol of formula

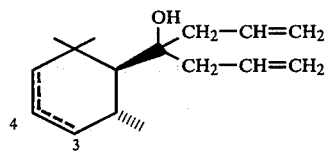 (I, trans)

is used as starting material to give trans-δ- and trans-ε-damascone.

3. Process according to claim 1, wherein a diallyl carbinol of formula

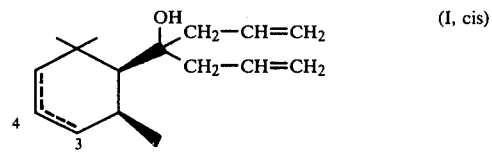 (I, cis)

is used as starting material to give cis-δ- and cis-ε-damascone.

4. Process according to any of the preceding claims wherein, the strong base is an alkali metal hydride, alkoxide or hydroxide.

5. Process according to claim 4, wherein the alkoxide is sodium or potassium tert-butoxide.

6. Process according to claim 5, wherein the reaction is effected by means of potassium tert-butoxide in dimethylformamide at a temperature of between about 20° and 70° C.

* * * * *